United States Patent [19]

Nichols et al.

[11] Patent Number: 4,705,902
[45] Date of Patent: Nov. 10, 1987

[54] DDTR-FREE 1,1-BIS(CHLOROPHENYL)-2,2,2-TRICHLOROETHANOL

[75] Inventors: Richard W. Nichols, Washington Crossing; William J. Zabrodski, Bensalem, both of Pa.; Abhijit Mitra, Westfield, N.J.

[73] Assignee: Rohm and Haas Company, Philadelphia, Pa.

[21] Appl. No.: 862,001

[22] Filed: May 15, 1986

Related U.S. Application Data

[60] Continuation-in-part of Ser. No. 783,392, Oct. 3, 1985, abandoned, which is a division of Ser. No. 740,618, Jun. 3, 1985, abandoned.

[51] Int. Cl.$^4$ .................. C07C 29/74; C07C 29/86
[52] U.S. Cl. .................. 568/810; 568/809; 568/812
[58] Field of Search ............... 568/810, 811, 812, 809

[56] References Cited

U.S. PATENT DOCUMENTS

| | | | |
|---|---|---|---|
| 2,686,816 | 8/1954 | Stoll et al. | 568/810 |
| 2,812,280 | 11/1957 | Wilson et al. | 568/810 |
| 2,812,362 | 11/1957 | Wilson et al. | 568/810 |
| 3,102,070 | 8/1963 | Riley et al. | 568/810 |
| 3,894,095 | 7/1975 | Cook et al. | 568/810 |
| 4,387,018 | 6/1983 | Cook et al. | 568/809 |

FOREIGN PATENT DOCUMENTS

| | | | |
|---|---|---|---|
| 831421 | 3/1960 | United Kingdom | 568/810 |
| 136346 | 7/1960 | U.S.S.R. | 568/810 |

OTHER PUBLICATIONS

Karr and Schiebel, "Fractional Liquid Extraction of 2,6-Lutidine, 3-Picoline, and 4-Picoline", 46, *Industrial and Engineering Chemistry*, 1583–1584 (1954).

Claveloux and Hodel, "Efficient Extraction Column Saves $143,000/yr.", 2 page brochure reprinted from mid-Nov. 1983 *Chemical Processing*.

Vol. III, *Technique of Organic Chemistry*, Part I Separation and Purification pp. 332–393 (2nd Ed. 1956).

*The Encyclopedia of Chemical Process Equipment*, edited by Mead, pp. 858–861 (1964).

Perry and Chilton, *Chemical Engineer's Handbook*, Fifth Ed., pp. 21-17 to 21-30.

Vol. 9, *Kirk–Othmer Encyclopedia of Chemical Technology*, Third Ed., pp. 672–721 (1980).

*Primary Examiner*—Werren B. Lone
*Attorney, Agent, or Firm*—Polly E. Ramstad

[57] ABSTRACT

Process for preparing DDTr-free 1,1-bis(chlorophenyl)-2,2,2-trichloroethanol (dicofol).

29 Claims, No Drawings

DDTR-FREE 1,1-BIS(CHLOROPHENYL)-2,2,2-TRICHLOROETHANOL

BACKGROUND OF THE INVENTION

This application is a continuation-in-part of U.S. patent application Ser. No. 783,392 filed Oct. 3, 1985 now abandoned which is a division of U.S. patent application Ser. No. 740,618 filed June 3, 1985 now abandoned.

This invention is directed to a process for preparing DDTr-free 1,1-bis(chlorophenyl)-2,2,2-trichloroethanol.

The 1,1-bis(halophenyl)-2,2,2-trichloroethanols are miticidal agents, the preparation of which is described in U.S. Pat. Nos. 2,812,280 and 2,812,362. 1,1-bis(chlorophenyl)-2,2,2-trichloroethanol (dicofol) is a commercial miticide and there are various pesticidal compositions which use it as an active ingredient.

The present commercial process for manufacturing 1,1-bis(chlorophenyl)-2,2,2-trichloroethanol (dicofol) uses 1,1-bis(chlorophenyl)-2,2,2-trichloroethane (DDT) as the starting material. DDT is dehydrohalogenated with alkali to afford 1,1-bis(chlorophenyl)dichloroethylene, which is chlorinated to afford 1,1-bis(chlorophenyl)-1,2,2,2-tetrachloroethane.

The 1,1-bis(chlorophenyl)-1,2,2,2-tetrachloroethane is then converted to the desired product, dicofol, by placing it in a hydrolysis reaction vessel with p-toluenesulfonic acid, sulfuric acid (99%) and water and then heating to about 110° C. Steam is injected into the reactor while continuing to heat the batch to about 140° C. Distillate from the reactor is monitored to ascertain an end point specific gravity of about 1.100 at 20° C. When the batch reaches about 140° C. and the specific gravity requirement is met, the batch continues to be heated to from about 143° C. to about 145° C. and water, in addition to steam, is added. The condensate continues to be monitored to an end point specific gravity of about 1.04 at 20° C. The batch is cooled to about 130° C., transferred to a hold tank, and allowed to settle for about 2 hours. The lower dicofol technical layer is separated and washed three times from about 95° C. to about 100° C. using about 0.3 pounds (lb.) of water per pound of dicofol technical. The batch is dehydrated at about 105° C. and 26 inches Hg vacuum to afford the desired dicofol technical.

Technical dicofol made by the present commercial process typically contains from about 2% to about 8% DDTr's.

The effectiveness of 1,1-bis(chlorophenyl)-2,2,2-trichloroethanol (dicofol) as an acaricide has encouraged extensive use of dicofol and compositions containing dicofol in agriculture and horticulture.

The DDT related impurities (DDTr's) which are encountered in the present commercial process used to manufacture dicofol include: 1,1-bis-(4-chlorophenyl)-2,2,2-trichloroethane (p,p'-DDT); 1-(4-chlorophenyl)-1-(2-chlorophenyl)-2,2,2-trichloroethane (o,p'-DDT); 1,1-bis-(4-chlorophenyl)-2,2-dichloroethylene (p,p'-DDE); 1-(4-chlorophenyl)-1-(2-chlorophenyl)-2,2-dichloroethylene (o,p'-DDE); 1,1-bis-(4-chlorophenyl)-2,2-dichloroethane (p,p'-DDD); 1-(4-chlorophenyl)-1-(2-chlorophenyl)-2,2-dichloroethane (o,p'-DDD); 1,1-bis-(4-chlorophenyl)-1,2,2,2-tetrachloroethane (p,p'-Cl-DDT); 1-(4-chlorophenyl-1-(2-chlorophenyl)-1,2,2,2-tetrachloroethane (o,p'-Cl-DDT). Non-DDTr impurities which are encountered in the present commercial process used to manufacture dicofol include: 4,4'-dichlorobenzophenone (p,p'-DCBP); 2,4'-dichlorobenzophenone (o,p'-DCBP); 4,4'-dichlorobenzil (p,p'-DCBZ); and 2,4'-dichlorobenzil (o,p'-DCBZ). DDTr's are present along with the desired dicofol product due to the impurity of DDT used as a starting reactant and formation during the conversion of DDT to dicofol. As a group, DDTr's are suspected of posing an environmental risk. Accordingly, it is desirable to find means to eliminate or reduce these DDTr impurities.

It is an object of this invention to prepare 1,1-bis(chlorophenyl)-2,2,2-trichloroethanol substantially free of DDTr's.

It is another object of this invention to furnish a process for making 1,1-bis(chlorophenyl)-2,2,2-trichloroethanol which is substantially free of DDTr's.

These and other objects of the invention will become apparent to those skilled in the art from the following description.

Unless otherwise stated, all percentages are by weight.

SUMMARY OF THE INVENTION

In accordance with the present invention, there is provided a practical process for producing DDTr free 1,1-bis-(chlorophenyl)-2,2,2-trichloroethanol by selective solvent extraction which comprises at a temperature of from about 31 5° C. to about 100° C.:

(a) dissolving technical 1,1-bis(chlorophenyl)-2,2,2-trichloroethanol in a hydroxylic solvent such as ($C_1$–$C_3$) alcohol, ($C_2$–$C_6$) diol, ($C_1$–$C_3$) organic acid, mixtures of said solvents, 4-hydroxy-3-methyl-2-butanone, or a solvent capable of affording a hydroxylic solvent mixture when mixed with water such as acetone, or mixtures of said solvents containing up to about 50% water to obtain a solution having a 1,1-bis(chlorophenyl)-2,2,2-trichloroethanol concentration of from about 1% to about 60%; and (b) extracting the solution with a straight, branched or cyclized ($C_4$–$C_{20}$)alkane; straight, branched or cyclized ($C_4$–$C_{20}$)alkene; straight, branched or cyclized ($C_6$–$C_{20}$)alkadiene; ($C_6$–$C_{10}$) single ring aromatic or mixtures thereof; and (c) separating the resulting layers; and (d) removing the solvent from the dicofol containing layer to afford the desired DDTr-free 1,1-bis(chlorophenyl)-2,2,2-trichloroethanol.

DETAILED DESCRIPTION OF THE INVENTION

The following diagram indicates the starting materials, intermediates, DDT related impurities and final product of the present process for preparing dicofol.

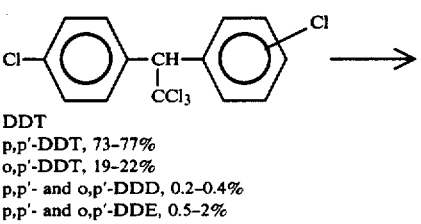

DDT
p,p'-DDT, 73–77%
o,p'-DDT, 19–22%
p,p'- and o,p'-DDD, 0.2–0.4%
p,p'- and o,p'-DDE, 0.5–2%

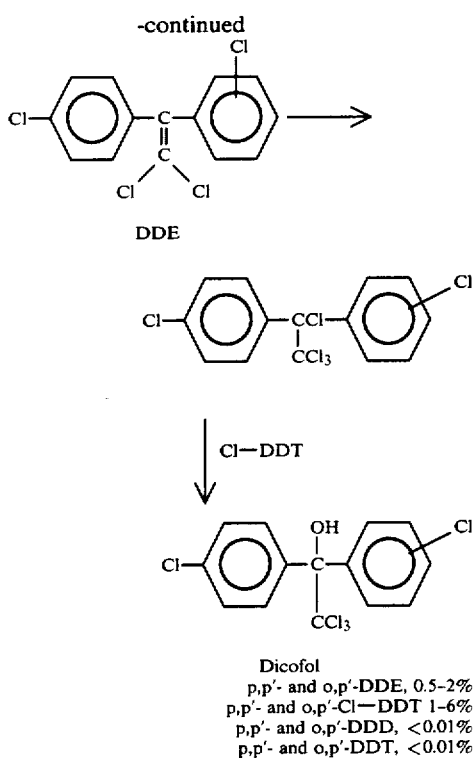

Dicofol
p,p'- and o,p'-DDE, 0.5-2%
p,p'- and o,p'-Cl—DDT 1-6%
p,p'- and o,p'-DDD, <0.01%
p,p'- and o,p'-DDT, <0.01%

The DDT used as a starting material typically contains from about 73% to about 77% p,p'-DDT; from about 19% to about 22% o,p'-DDT; and from about 0.2 to about 0.4% p,p'- and o,p'-DDD.

The conversion of DDT to DDE is an efficient reaction and typically the dicofol produced will contain less than 0.01% DDT. However, non-ideal reaction conditions can result in higher levels of DDT-contaminated DDE and, consequently, result in higher levels of DDT in the dicofol product.

In practice, conversion of DDE to Cl-DDT of greater than 99% is difficult to achieve. Therefore, Cl-DDT typically contains from about 0.5% to about 2% DDE. Further, since chlorination of o,p'-DDE to form o,p'-Cl-DDT is significantly slower than chlorination of p,p'-DDE to form p,p'-Cl-DDT (approximately 50 times slower) the bulk of the residual DDE in the Cl-DDT produced is o,p'-DDE. Dicofol technical typically contains from about 0.5% to about 2% DDE, both o,p'- and p,p'-DDE.

In the hydrolysis of Cl-DDT to dicofol, a point is reached beyond which further conversion of Cl-DDT becomes very slow. This is believed to be due to a mode of dicofol degradation that yields Cl-DDT. As the abovementioned point is approached, other dicofol degradation products accumulate in the batch. These degradation products include DCBP and DCBZ. Dicofol technical typically contains o,p'-Cl-DDT and p,p'-Cl-DDT at levels of from about 1% to about 6%.

It has now been discovered that DDTr's can be efficiently eliminated from dicofol technical by "selective solvent extraction."

The dicofol prepared by the present invention is free of DDTr's, that is, it contains less than 0.1% of DDTr's.

Removal of the DDTr's from dicofol is accomplished by "selective solvent extraction." "Selective solvent extraction" means unequal distribution of dicofol and DDTr's between two particular liquid phases to prepare DDTr free dicofol. Generally, this extraction may be accomplished by continuous liquid-liquid contercurrent extraction or by sequential batch extraction.

For economic reasons, where DDTr's are present at from about 1% or higher, this extraction may preferably be accomplished by means of continuous liquid-liquid counter-current extraction; where DDTr levels are below about 1%, then this extraction may preferably be accomplished by means of batch extraction.

It has been found that DDTr removal from dicofol technical may be accomplished by employing limited classes of solvents. Hydrocarbons in general and in particular straight, branched or cyclized ($C_4$–$C_{20}$)alkanes such as hexane, heptane, octane, isooctane, cyclohexane and the like; straight, branched or cyclized ($C_4$–$C_{20}$)alkenes such as diisobutylene, cyclohexene and the like; straight, branched or cyclized ($C_6$–$C_{20}$) cumulated, conjugated or isolated alkadienes such as dicyclopentadiene and the like; ($C_6$–$C_{10}$) single ring aromatics such as benzene, toluene, xylene, cumene and the like; or mixtures of said solvents may be used as one of the liquid phases ("extracting solvent phase") in selective solvent extraction. The second liquid phase ("raffinate phase") is limited to water miscible solvents including but not limited to hydroxylic solvents such as ($C_1$–$C_3$) alcohols, for example, methanol and ethanol and the like; ($C_2$–$C_6$) diols, for example, ethylene glycol, 1,3-butanediol, 2,5-hexanediol and the like; ($C_1$–$C_3$) organic acids, for example, acetic acid, formic acid and the like; 4-hydroxy-3-methyl-2-butanone; or a solvent capable of affording a hydroxylic solvent mixture when mixed with water, for example, acetone and the like; or mixtures of the above solvents. Typically, the raffinate phase will be the lower layer, although with particular solvents, it may be the upper layer.

Separation between the two phases is preferably aided by the addition of water. The actual amount of water used varies depending upon the selection of solvents and concentration of dicofol technical. Generally, up to about 50% water may be used. The precise amount of water used with a given pair of solvents (raffinate phase solvent and extracting phase solvent) can readily be determined by one skilled in the art.

Temperatures in the range of from about −5° C. to about 100° C. may be used. The actual temperature employed will depend on the selection of solvents and will be apparent to one skilled in the art after making the selection of solvents for the two liquid phases.

Depending on the selection of solvents, it may be necessary to employ pressure during extraction. The amount of pressure required will depend on the selection of solvents and will be apparent to one skilled in the art.

Dicofol technical is dissolved in the aqueous solvents (raffinate phase) preparatory to the extraction of DDTr's. The dicofol concentration in such solutions will generally be from about 1% to about 60%.

Preferably, the extracting solvent phase will comprise ($C_5$–$C_{16}$)alkanes or ($C_5$–$C_{15}$)alkenes or mixtures thereof and most preferably mixed heptanes having a boiling point in the range of from about 91° to about 97° C.

Preferably, the raffinate phase will comprise aqueous methanol (87–93%); ethanol (70–85%); or ($C_2$–$C_6$) diols with 0–10% water and the most preferable being aqueous methanol.

In the case of methanol specifically, the amount of water employed will most preferably be in the range of from about 9% to about 13%.

Preferably, the temperature employed is between from about 10° C. to about 60° C. and, most preferably, between from about 20° C. to about 40° C.

Preferably the dicofol concentration employed is between from about 10% to about 50% and, most preferably, between from about 25% to about 35%.

EXTRACTION OF DDTR'S FROM DICOFOL TECHNICAL USING N-HEPTANE AND 90% METHANOL—10% WATER (90% AQUEOUS METHANOL)

The results of this experiment are set forth below in Tables I, II and III. Table I shows the physical data of the system (volume, weight and concentrated weight). Table II shows the reported analytical results. Table III shows the calculated results, based on the analytical data, for recovery of dicofol and the percentage of DDTr's removed. The terms "partition coefficient" and "distribution coefficient" are used interchangeably herein.

A 50 g sample of the desired dicofol solution was taken in a stoppered 100 ml graduated cylinder. The initial volumes were recorded (Table I—Column 1). n-Heptane (20 g.) was added to all samples and stoppered. They were then shaken well for two minutes. The samples were placed in an ice-water bath for 30 minutes. After the cooling period all samples were again shaken for 2 minutes. The samples were returned to the bath and allowed to equilibrate for 30 minutes. The samples were then removed from the bath and volumes recorded (Table I—Columns 2 and 3). The layers were then separated and each layer weighed (Columns 4 and 5). The separated layers were concentrated under vacuum (70° C., 1 mm Hg), weighed (columns 6 and 7) and analyzed (Table II).

The results (Table III) demonstrate that the DDTr fraction was preferentially extracted by n-heptane.

TABLE I

| Partition of Dicofol Technical Between n-Heptane and 90% Aqueous Methanol at 0° C.[1] | | | | | | |
|---|---|---|---|---|---|---|
| Dicofol Solution (Volume) | Heptane Layer Volume | Methanol Layer Volume | Heptane Layer Weight | Methanol Layer Weight | Heptane Layer Weight (Stripped) | Methanol Layer Weight (Stripped) |
| 50% (47.0 ml) | 22 ml | 53 ml | 16.29 g | 52.68 g | 1.72 g | 22.77 g |
| 33% (52.0 ml) | 24.5 ml | 55.5 ml | 17.62 g | 51.38 g | 1.44 g | 14.81 g |
| 16.7% (57.5 ml) | 25.5 ml | 59.5 ml | 18.18 g | 51.48 g | 0.91 g | 7.43 g |
| 8.4% (59.5 ml) | 26.5 ml | 61.0 ml | 18.19 g | 51.44 g | 0.46 g | 3.66 g |
| 4.2% (60.5 ml) | 26.5 ml | 62.0 ml | 17.94 g | 51.21 g | 0.24 g | 1.79 g |

[1]20 g (29.4 ml) n-heptane and 50 g dicofol solution were used.

TABLE II

| | Dicofol Solution | OP' DCBP | OP' DCBZ | PP' DCBP | PP' DCBZ | OP' Dicofol | PP' Dicofol | OP' DDE | PP' DDE | OP' Cl-DDT | PP' Cl-DDT | % DDTR's | Accountability |
|---|---|---|---|---|---|---|---|---|---|---|---|---|---|
| A | 50% | 1.5 | 1.7 | 1.7 | 0.6 | 7.1 | 51.7 | 4.8 | 1.0 | 0.4 | 3.4 | 9.6 | 81.0 |
| Heptane | 33% | 1.5 | 1.8 | 1.5 | 0.7 | 6.0 | 47.3 | 5.2 | 1.6 | 1.2 | 3.4 | 11.4 | 77.0 |
| layer | 16.7% | 1.5 | 1.9 | 1.6 | 0.9 | 5.3 | 45.6 | 5.5 | 1.4 | 1.1 | 4.0 | 12.0 | 76.1 |
| | 8.4% | 1.6 | 2.0 | 1.5 | 1.0 | 5.5 | 47.1 | 6.1 | 1.3 | 0.7 | 5.1 | 13.2 | 79.7 |
| | 4.2% | 1.9 | 2.4 | 1.6 | 1.7 | 5.3 | 48.0 | 6.2 | 1.2 | 0.8 | 5.5 | 13.7 | 83.0 |
| | Starting Dicofol | 1.0 | 1.5 | 0.6 | 0.33 | 13.0 | 74.6 | 1.1 | 0.2 | 0.1 | 0.9 | 2.3 | 96.0 |
| B | 50% | 1.8 | 1.1 | 1.3 | 0.5 | 12.9 | 74.2 | 0.9 | 0.1 | 0.1 | 0.5 | 1.6 | 94.7 |
| Aqueous | 33% | 1.7 | 1.2 | 1.3 | 0.3 | 12.8 | 73.4 | 0.8 | 0.1 | 0.1 | 0.4 | 1.4 | 93.8 |
| Methanol | 16.7% | 1.6 | 1.0 | 1.5 | 0.5 | 13.3 | 76.3 | 0.6 | 0.1 | 0.1 | 0.3 | 1.1 | 97.1 |
| layer | 8.4% | 1.6 | 1.0 | 1.4 | 0.4 | 13.2 | 76.4 | 0.6 | 0.1 | 0.1 | 0.2 | 1.1 | 96.9 |
| | 4.2% | 1.8 | 0.9 | 1.2 | 0.4 | 13.8 | 78.2 | 0.5 | .05 | 0.3 | 0.2 | 1.0 | 99.0 |

TABLE III

| Calculated Results from 90% Aqueous Methanol Solution, 0° C. | | | | |
|---|---|---|---|---|
| Dicofol Solutions | Recovered Weight (%) | % DDTR's Removed | % p,p'-Dicofol Recovered | % o,p'-Dicofol Recovered |
| 50% | 93.0 | 31 | 95.0 | 96.0 |
| 33% | 91.1 | 45 | 94.1 | 95.6 |
| 16.7% | 89.1 | 57 | 93.2 | 95.3 |
| 8.4% | 88.8 | 60 | 92.8 | 95.0 |
| 4.2% | 88.2 | 65 | 92.4 | 95.1 |

In subsequent experiments, the partitioning of dicofol technical between n-heptane and 90% aqueous methanol was also evaluated at 23° C. The combined results from the 0° C. and 23° C. experiments are presented in Table IV where the results are expressed as distribution coefficients for dicofol and the two principal DDTr's found in dicofol technical, o,p'-DDE and p,p'-Cl-DDT. In all cases, the extractability of DDTr's exceeded that of dicofol by a significant margin.

TABLE IV

Distribution Coefficients[1] and Selectivities[2] from Extraction Experiments

| Conc. of Aq.[3] Dicofol Sol'n | Heptane (grams) | Temp. °C. | o,p' and p,p' Dicofol[4] D.C. | o,p' DDE D.C. | o,p' DDE Sel. | p,p' Cl-DDT D.C. | p,p' Cl-DDT Sel. |
|---|---|---|---|---|---|---|---|
| 50 | 20 | 0 | .16 | 1.3 | 7.9 | 1.5 | 9.4 |
|    | 40 | 23 | .31 | 1.66 | 5.3 | 2.1 | 6.8 |
| 40 | 40 | 23 | .32 | 2.32 | 7.2 | 2.8 | 8.6 |
| 33 | 20 | 0 | .17 | 1.8 | 10.5 | 2.6 | 14.9 |
| 30 | 40 | 23 | .30 | 2.4 | 7.9 | 4.0 | 13.1 |
| 20 | 40 | 23 | .31 | 3.5 | 11.0 | 5.3 | 16.8 |
| 16.7 | 20 | 0 | .20 | 3.2 | 16.1 | 4.4 | 22.4 |
|    | 20 | 23 | .33 | 3.4 | 10.1 | 4.1 | 12.2 |
| 10 | 40 | 23 | .32 | 3.9 | 12.2 | 7.5 | 23.4 |
| 8.4 | 20 | 0 | .21 | 3.6 | 17.3 | 9.1 | 23.3 |

[1]Distribution coefficient (D.C.): grams of solute per gram of extract layer (heptane) divided by grams of solute per gram of raffinate layer.
[2]Selectivity (Sel.): Ratio of DDTr distribution coefficient to that of dicofol.
[3]All dicofol solutions made up with 90% aqueous methanol; 50 g of solution used in each extraction.
[4]The distribution coefficients of o,p' and p,p' dicofol are essentially the same.

Another series of extraction experiments was done to demonstrate that p,p'-DDT and p,p'-DDD, DDTr's, not normally present in significant amounts in dicofol, could be removed by the extraction approach. These experiments are summarized in Table V, which shows that p,p'-DDT is very preferentially extracted by n-heptane and p,p'-DDD, while not so easily extracted, is also preferentially removed.

TABLE V

Distribution Coefficients for p,p'-DDT and p,p'-DDD

| % DDD,[1,2] DDT (Wt %) | D.C. Dicofol | o,p'-DDE D.C. | o,p'-DDE Sel. | p,p'-ClDDT D.C. | p,p'-ClDDT Sel. | p,p'-DDD D.C. | p,p'-DDD Sel. | p,p'-DDT D.C. | p,p'-DDT Sel. |
|---|---|---|---|---|---|---|---|---|---|
| 0.25 | .31 | 2.4 | 7.6 | 3.7 | 11.8 | 0.66 | 2.1 | 1.9 | 5.9 |
| 0.72 | .33 | 2.4 | 7.2 | 3.8 | 11.4 | 0.71 | 2.1 | 1.9 | 5.6 |
| 1.80 | .35 | 2.4 | 6.8 | 3.8 | 10.8 | 0.79 | 2.2 | 2.1 | 6.0 |

[1]As a percentage of dicofol technical. Extractions used 50 g of 33% solution of dicofol technical in 90% aqueous methanol contacted with 40 g of n-heptane at 23° C.
[2]Dicofol technical containing usual quantities of o,p'-DDE and p,p'-Cl-DDT was spiked with three levels of p,p'-DDD and separately with three levels of p,p'-DDT.

The effect on distribution coefficients and selectivities of the amount of water in the methanol was determined. Results of this study are presented in Table VI. As can be seen, the percentage of water used has an effect on all monitored materials in the system. All distribution coefficients rise as the percentage of water increases. The selectivities rise initially but then begin to decrease at water levels higher than a maximum range. Importantly, if the water in the methanol is omitted, the addition of practical concentrations of dicofol technical causes the phases to coalesce.

TABLE VI

Effect of Water Content on Distribution Coefficients and Selectivities

| % H₂O in Aq. MeOH[1] | D.C. Dicofol | o,p'-DDE D.C. | o,p'-DDE Sel. | p,p'-Cl-DDT D.C. | p,p'-Cl-DDT Sel. |
|---|---|---|---|---|---|
| 4 | .27 | 1.5 | 5.7 | 1.9 | 7.0 |
| 8 | .29 | 2.2 | 7.7 | 2.9 | 10.1 |
| 12 | .38 | 3.1 | 8.3 | 4.6 | 12.2 |
| 16 | .60 | 3.6 | 6.1 | 6.8 | 11.4 |

[1]Single stage extractions conducted by contacting 50 g of 33% solution of dicofol technical in various aqueous methanols with 40 g of n-heptane at 23° C.

Alternative solvent systems were evaluated. The distribution coefficients were determined by partitioning dicofol technical.

In Table VII, n-heptane was used as the extractant and different raffinate phase solvents were evaluated. In Table VIII, ethanol was used as the raffinate solvent and different extracting solvents were evaluated. In Table IX, n-heptane was used as the extractant and ethanol at different aqueous concentrations was used as the raffinate solvent. In the experiments set forth in Table IX, 30% dicofol technical solution (in the raffinate layer) was used and 50 grams of this solution was partitioned with 40 grams of the extracting solvent. In Table X, methanol was used as the raffinate solvent and different extracting solvents were evaluated. And in Table XI, using n-heptane as the extracting solvent and aqueous methanol as the raffinate solvent, the partition coefficients were determined as a function of temperature and concentration of dicofol.

TABLE VII

Dicofol and DDTr Partition Coefficients
Distributions Between n-Heptane and Reffinate Solvents

| Solvent | Parts Solvent | Parts Water | Parts n-Heptane | Parts Dicofol | Partition Coeff. Dicofol | Partition Coeff. o,p'-DDE | Partition Coeff. p,p'-Cl-DDT |
|---|---|---|---|---|---|---|---|
| Acetic Acid-Methanol | 3.5 31.5 | 0.0 | 30 | 15 | 0.33 | 1.11 | 1.40 |
| Acetone | 30 | 3.4 | 30 | 2.25 | 3.40 | 6.43 | 11.14 |

TABLE VII-continued

Dicofol and DDTr Partition Coefficients
Distributions Between n-Heptane and Reffinate Solvents

| Solvent | Parts Solvent | Parts Water | Parts n-Heptane | Parts Dicofol | Partition Coeff. Dicofol | Partition Coeff. o,p'-DDE | Partition Coeff. p,p'-Cl-DDT |
|---|---|---|---|---|---|---|---|
| 1,3-Butanediol | 20 | 0.0 | 30.1 | 7.6 | 0.15 | 6.02 | 6.15 |
| 1,3-Butanediol | 10 | 1.1 | 30 | 4 | 0.84 | 26.60 | 35.32 |
| Ethylene Glycol | 25 | 0.0 | 30 | 4 | 1.20 | 121.40 | 79.49 |
| Formic Acid | 42.99 | 4.51 | 40 | 2.6 | 28.17 | 191.98 | 254.77 |
| Formic Acid-Methanol | 3.17 31.5 | 0.33 | 30 | 15 | 0.31 | 1.49 | 1.99 |
| 2,5-Hexanediol | 14.5 | 0.0 | 30.2 | 4.0 | 0.21 | 3.86 | 5.24 |
| 4-hydroxy-3-methyl-2-butanone | 24 | 3.1 | 30.1 | 4.0 | 0.15 | 2.85 | 4.78 |
| Isopropanol | 30 | 7.7 | 30 | 2.45 | 1.50 | 2.46 | 3.40 |
| Propionic Acid | 20 | 6.5 | 20 | 5 | 6.60 | 21.82 | 38.92 |

TABLE VIII

Dicofol and DDTr Distribution Coefficients
Distributions Between Aqueous Ethanol and Extraction Solvents

| Solvent | Parts Solvent | Parts Water | Parts Ethanol | Parts Dicofol | Partition Coeff. Dicofol | Partition Coeff. o,p'-DDE | Partition Coeff. p,p'-Cl-DDT |
|---|---|---|---|---|---|---|---|
| Cyclohexene | 40 | 11.5 | 29.6 | 8.9 | 8.3 | 25 | 50 |
| 2,4,4-Trimethyl-1-pentene | 40 | 11.5 | 29.6 | 8.9 | 3.82 | 14.0 | 27.2 |
| n-Heptane | 30 | 11.5 | 29.6 | 8.9 | 1.88 | 9.31 | 16.3 |
| Ligroine (b.p. 90-110° C.) | 40 | 11.5 | 29.6 | 8.9 | 2.22 | 10.8 | 20.7 |
| Petroleum Ether (b.p. 37-57° C.) | 30 | 11.5 | 29.6 | 8.9 | 2.04 | 7.89 | 12.3 |

TABLE IX

Results of Extractions with Various Concentrations of Aqueous Ethanol
Distribution Coeff. & Selectivities using Heptane at 23° C.

| Upper Layer | Aqueous Ethanol | Conc. of Dicofol | o,p'-p,p' dicofol D.C. | o,p'-DDE D.C. | o,p'-DDE Sel. | p,p' Cl-DDT D.C. | p,p' Cl-DDT Sel. |
|---|---|---|---|---|---|---|---|
| Heptane | 95% | 30% | | MISCIBLE | | | |
| Heptane | 90% | 30% | 0.76 | 1.08 | 1.42 | 0.91 | 1.20 |
| Heptane | 87% | 30% | 0.63 | 1.28 | 2.01 | 1.48 | 2.33 |
| Heptane | 85% | 30% | 0.74 | 2.06 | 2.78 | 1.65 | 2.22 |

TABLE X

Dicofol and DDTr Distribution Coefficient
Distribution Between Aqueous Methanol and Extraction Solvents

| Solvent | Parts Solvent | Parts Water | Parts Methanol | Parts Dicofol | Partition Coeff. Dicofol | Partition Coeff. o,p'-DDE | Partition Coeff. p,p'-Cl-DDT |
|---|---|---|---|---|---|---|---|
| Cyclohexane | 40 | 3.5 | 31.5 | 15 | 1.00 | 4.66 | 5.48 |
| Cyclohexene | 40 | 5.25 | 29.75 | 15 | 4.17 | 20 | 50 |
| Cyclohexene | 40 | 3.5 | 31.5 | 15 | 1.89 | 5.88 | 10 |
| Decalin | 40 | 3.5 | 31.5 | 15 | 1.04 | 8.3 | 20 |
| 2,4,4-tri-methyl-1-pentene | 40 | 5.25 | 29.75 | 15 | 1.33 | 6.43 | 10.0 |
| 2,4,4-tri-methyl-1-pentene | 40 | 3.5 | 31.5 | 15 | 0.77 | 3.00 | 4.93 |
| 2,4,4-tri-methyl-1-pentene | 40 | 1.75 | 33.25 | 15 | 0.64 | 0.39 | 1.88 |
| n-Eicosane/n-Heptane | 15 15 | 3.5 | 31.5 | 15 | 0.22 | 2.45 | 4.04 |
| 1-Eicosene/n-Heptane | 25.1 5 | 3.55 | 31.94 | 15.21 | 0.28 | 3.08 | 5.44 |
| Mixed Heptanes[1] | 40 | 3.5 | 31.5 | 15 | 0.40 | 3.79 | 9.48 |
| n-Hexadecane | 30 | 3.5 | 31.5 | 15 | 0.41 | 5.31 | 9.75 |
| Laktane[2] | 40 | 3.5 | 31.5 | 15 | 1.04 | 3.53 | 2.94 |
| Ligroine | 30 | 5.25 | 29.75 | 15 | 0.60 | 4.82 | 6.47 |

TABLE X-continued

Dicofol and DDTr Distribution Coefficient
Distribution Between Aqueous Methanol and Extraction Solvents

| Solvent | Parts Solvent | Parts Water | Parts Methanol | Parts Dicofol | Partition Coeff. Dicofol | Partition Coeff. o,p'-DDE | Partition Coeff. p,p'-Cl-DDT |
|---|---|---|---|---|---|---|---|
| Ligroine (b.p. 90–110° C.) | 30 | 3.5 | 31.5 | 15 | 0.34 | 2.75 | 3.69 |
| Ligroine (b.p. 90–110° C.) | 30 | 1.75 | 33.25 | 15 | 0.29 | 1.82 | 2.41 |
| 4-methyl-cyclo-hexene (b.p. 90–110° C.) | 40 | 3.5 | 31.5 | 15 | 1.69 | 5.88 | 11.1 |
| Octenes (−1 and −2)[3] | 30 | 3.5 | 31.5 | 15 | 0.84 | 3.82 | 5.95 |
| 1-Pentadecene | 19.6 | 3.5 | 31.5 | 15 | 0.41 | 4.30 | 6.53 |
| 2-Pentene | 24.2 | 1.4 | 12.6 | 6 | 1.06 | 3.41 | 4.64 |
| Petroleum ether (b.p. 37–57° C.) | 30 | 5.25 | 29.75 | 15 | 0.49 | 4.22 | 6.69 |
| Petroleum ether (b.p. 37–57° C.) | 30 | 3.5 | 31.5 | 15 | 0.34 | 1.69 | 2.20 |
| Petroleum ether (b.p. 37–57° C.) | 30 | 1.75 | 33.25 | 15 | 0.33 | 1.37 | 1.77 |
| Toluene | 36 | 8.55 | 36.45 | 5.0 | 7.45 | 34.2 | 59.9 |
| Toluene/ n-Heptane | 20 20 | 3.5 | 31.5 | 15 | 1.27 | 3.01 | 3.47 |
| 2,2,4-tri-methylpentane | 40 | 3.5 | 31.5 | 15 | 0.27 | 2.06 | 2.24 |

[1] Purchased from Union Oil Co. as "Heptane 1483", b.p. range 92.3° to 96.0° C., composed primarily of $C_7$ saturated hydrocarbons.
[2] Laktane is a commercial hydrocarbon mixture containing approximately 30% toluene.
[3] Practical grade from Eastman Kodak.

TABLE XI

Distribution of Dicofol and DDTr+s
Effects of Temperature and Concentration
(Aqueous Methanol and n-Heptane System)

| Solvent | Parts Solvent | Parts Water | Parts Methanol | Parts Dicofol | Temper. °C. | Partition Coeff. Dicofol | Partition Coeff. o,p'-DDE | Partition Coeff. p,p'-Cl-DDT |
|---|---|---|---|---|---|---|---|---|
| n-Heptane | 40 | 4.5 | 40.5 | 5 | 23 | 0.32 | 3.91 | 7.52 |
| n-Heptane | 40 | 3.5 | 31.5 | 15 | 23 | 0.30 | 2.41 | 3.98 |
| n-Heptane | 40 | 3 | 27 | 20 | 23 | 0.32 | 2.32 | 2.78 |
| n-Heptane | 40 | 2.5 | 22.5 | 25 | 23 | 0.31 | 1.66 | 2.13 |
| n-Heptane | 40 | 4.5 | 40.5 | 5 | 35 | 0.44 | 4.40 | 8.31 |
| n-Heptane | 40 | 3.5 | 31.5 | 15 | 35 | 0.39 | 2.56 | 3.27 |
| n-Heptane | 40 | 3 | 27 | 20 | 35 | 0.43 | 1.90 | 2.95 |
| n-Heptane | 40 | 2.5 | 22.5 | 25 | 35 | 0.44 | 1.90 | 2.08 |

A laboratory simulation of a continuously operated countercurrent extraction column was accomplished by modeling with an extended series of individual batch extractions. A six stage column having four extraction stages and two backwash stages was found to afford a high degree of DDTr extraction and permit a high level of dicofol recovery (greater than 90%) having increased purity (greater than 92%). The experiment involved batch extractions using 50 g of 90% aqueous MeOH/dicofol solutions (40% technical); 50 g n-heptane portions; and 20 g 90% aqueous MeOH solutions for the backwash. The dicofol feed solutions were mixed with aqueous backwash that had contacted exiting heptane extracts, and were then extracted in counter current manner three times with heptane extracts and then a final time with entering fresh heptane. Results of this analysis are presented in Table XII.

TABLE XII

Batch Simulation of Continuous Counter Current Distribution:
Four Extraction Stages, Two Backwash Stages at 23° C.
Analysis of Purified Dicofol Concentrate

| Component | Dicofol Feed | Product |
|---|---|---|
| pp DCBZ | 0.3 | .13 |
| op' Dicofol | 13.0 | 14.3 |
| pp' Dicofol | 70.3 | 77.9 |
| op' DDE | 0.9 | 0.04 |
| pp' DDE | 0.09 | —[1] |
| op' Cl-DDT | 0.20 | — |
| pp' Cl-DDT | 3.4 | 0.1 |
| % DDTr | 4.6 | 0.14 |
| Sample Weight | 20.0 | 16.87 |
| Dicofol Recovery, % |  | 93% |

[1] Not detected.

To establish commercial feasibility a pilot plant scale demonstration was conducted. At the conclusion of the pilot trials, a "production run" was made to demonstrate extended operations. More than one hundred pounds of dicofol was purified in this run. Approximately 98% of the dicofol was recovered.

Pilot plant production run purifications of dicofol were done in a Karr reciprocatory plate extraction column under the conditions listed below in Table XIII.

As the feed solution passes through the column, it intimately mixes with a non-polar hydrocarbon solvent. By introducing the feed at the midpoint of the column, the backwash stream recaptures dicofol that has transferred to the hydrocarbon solvent phase.

TABLE XIII

| Dicofol Purification Production Run Conditions | |
|---|---|
| Column diameter | one inch |
| Weight concentration of dicofol | 32.57% |
| Feed rate | 87 g/minute |
| Solvent rate | 90 g/minute |
| Backwash rate | 55 g/minute |
| Total column flow | 860 gal/hr./ft.$^2$ |
| Temperature | 35° C. |
| Column agitator strokes | 50/minute |

A detailed analysis of the dicofol made in the "production run" is presented in Table XIV where it is contrasted with the dicofol technical before extraction. DDTr's were reduced from about 5.5% to less than 0.1% by removal of DDE and Cl-DDT isomers. The extent of removal was greater than the removal achieved in laboratory modeling trials (4.6% reduced to 0.15%). A significant increase in active ingredient content (from about 85% to about 96% was achieved. No significant change in the proportions of the two dicofol isomers occurs.

TABLE XIV

| Purification of Dicofol in Pilot Plant | | |
|---|---|---|
| Component | Before[1] | After[2] |
| Active Ingredient | | |
| p,p'-Dicofol | 70.7% | 80.7% |
| o,p'-Dicofol | 14.0% | 15.4% |
| Total Dicofol | 84.7% | 96.1% |
| DDTr Impurities | | |
| p,p'-DDT | <.01% | <5 ppm |
| o,p'-DDT | <.01% | <5 ppm |
| p,p'-DDE | 0.1% | <5 ppm |
| o,p'-DDE | 1.3% | 84 ppm |
| p,p'-DDD | <.01% | <5 ppm |
| o,p'-DDD | <.01% | <5 ppm |
| p,p'-ClDDT | 3.9% | 15 ppm |
| o,p'-ClDDT | 0.2% | 90 ppm |
| Total DDTr's | 5.5% | 190–225 ppm (0.02%) |
| Non-DDTr Impurities | | |
| p,p'-DCBP | 0.3% | 0.4% |
| o,p'-DCBP | 0.5% | 0.2% |
| p,p'-DCBZ | 0.2% | 0.14% |
| o,p'-DCBZ | 1.0% | 1.0% |
| Total Non-DDTr's | 2.0% | 1.7% |
| Unidentified Ingredients | 7.8% | 1.9%[3] |
| Total Components | 100.0 | 100.0 |

[1]Composition of dicofol technical used in pilot trials.
[2]Limit of detection for DDTr's = 5 ppm.
[3]Polar materials unrelated to DDT.

We claim:

1. A process for preparing DDTr-free 1,1-bis(chlorophenyl)-2,2,2-trichloroethanol from technical 1,1-bis(chlorophenyl)-2,2,2-trichloroethanol which comprises at a temperature of from about −5° C. to about 100° C.:
   (a) dissolving technical 1,1-bis(chlorophenyl)-2,2,2-trichloroethanol in a solvent selected from the group ($C_1$–$C_3$) alcohol, ($C_2$–$C_6$) diol, ($C_1$–$C_3$) organic acid, 4-hydroxy-3-methyl-2-butanone, acetone, or mixtures thereof containing up to about 50% water to obtain a solution having a 1,1-bis(chlorophenyl)-2,2,2-trichloroethanol concentration of from about 1% to about 60%; and
   (b) extracting the solution with a solvent selected from ($C_4$–$C_{20}$)alkane, ($C_4$–$C_{20}$)alkene, ($C_6$–$C_{20}$)alkadiene, ($C_6$–$C_{10}$) single ring aromatic, or mixtures thereof; and
   (c) separating the resulting layers; and
   (d) removing the solvent from the dicofol containing layer to afford the desired DDTr-free 1,1-bis(chlorophenyl)-2,2,2-trichloroethanol.

2. The process of claim 1 wherein the extraction is continuous.

3. The process of claim 1 wherein DDTr's present with 1,1-bis(chlorophenyl)-2,2,2-trichloroethanol is less than about 0.1%.

4. The process of claim 1 wherein 1,1-bis(chlorophenyl)-2,2,2-trichloroethanol is dissolved in methanol, ethanol, ($C_2$–$C_6$) diol or mixtures thereof containing up to about 30% water to obtain a solution having a 1,1-bis(chlorophenyl)-2,2,2-trichloroethanol concentration of from about 10% to about 50%.

5. The process of claim 4 wherein said solution is extracted with a ($C_5$–$C_{16}$)alkane, ($C_5$–$C_{15}$)alkene or mixtures thereof.

6. The process of claim 4 wherein 1,1-bis(chlorophenyl)-2,2,2-trichloroethanol is dissolved in methanol.

7. The process of claim 5 wherein said process is carried out between about 10° C. and about 60° C.

8. The procss of claim 5 wherein mixed heptanes are employed.

9. The process of claim 6 wherein methanol containing from about 7% to about 13% water is employed.

10. The process of claim 9 wherein methanol containing from about 9% to about 13% water is employed.

11. The process of claim 10 wherein said process is carried out between about 20° C. and about 40° C.

12. A process for preparing DDTr-free 1,1-bis(chlorophenyl)-2,2,2-trichloroethanol from technical 1,1-bis(chlorophenyl)-2,2,2-trichloroethanol which comprises at a temperature of from about 10° C. to about 60° C.:
   (a) dissolving technical 1,1-bis(chlorophenyl)-2,2,2-trichloroethanol in a solvent selected from methanol, ethanol, ($C_2$–$C_6$) diol or mixtures thereof containing up to about 30% water to obtain a solution having a 1,1-bis(chlorophenyl)-2,2,2-trichloroethanol concentration of from about 10% to about 50%; and
   (b) extracting the solution with a solvent selected from ($C_5$–$C_{16}$)alkane, ($C_5$–$C_{15}$)alkene or mixtures thereof; and
   (c) separating the resulting layers; and
   (d) removing the solvent from the dicofol containing layer to afford the desired DDTr-free 1,1-bis(chlorophenyl)-2,2,2-trichloroethanol.

13. The process of claim 12 wherein the extraction is continuous.

14. A process for preparing DDTr-free 1,1-bis(chlorophenyl)-2,2,2-trichloroethanol from technical 1,1-bis(chlorophenyl)-2,2,2-trichloroethanol which comprises at a temperature of from about 20° C. to about 40° C.:
   (a) dissolving technical 1,1-bis(chlorophenyl)-2,2,2-trichloroethanol in aqueous methanol containing from about 9% to about 13% water to obtain a solution having a 1,1-bis(chlorophenyl)-2,2,2-trichloroethanol concentration of from about 25% to about 35%; and
   (b) extracting the solution with mixed heptanes; and
   (c) separating the resulting layers; and
   (d) removing the solvent from the dicofol containing layer to afford the desired 1,1-bis(chlorophenyl)-

2,2,2-trichloroethanol having less than 0.1% DDTr's.

15. The process of claim 14 wherein said extraction is by continuous liquid-liquid countercurrent extraction.

16. A process for preparing DDTr-free 1,1-bis(chlorophenyl)-2,2,2-trichloroethanol comprising a liquid-liquid extraction conducted at a temperature of from about $-5°$ C. to about $100°$ C. by:

dissolving DDTr-containing 1,1-bis(chlorophenyl)-2,2,2-trichloroethanol in a solvent selected from the group consisting of ($C_1$–$C_3$) alcohol, ($C_2$–$C_6$) diol, ($C_1$–$C_3$) organic acid, 4-hydroxy-3-methyl-2-butanone, acetone, and mixtures thereof containing up to about 50% water to obtain a solution having a 1,1-bis(chlorophenyl)-2,2,2-trichloroethanol concentration of from about 1% to about 60%; and extracting the DDTr's from the solution with another solvent selected from the group consisting of ($C_4$–$C_{20}$)alkane, ($C_4$–$C_{20}$)alkene, ($C_6$–$C_{20}$)alkadiene, ($C_6$–$C_{10}$)single ring aromatic, and mixtures thereof to obtain the DDTr-free 1,1-bis(chlorophenyl)-2,2,2-trichloroethanol.

17. The extraction process of claim 16 wherein the resulting layers are separated and the solvent is removed from the 1,1-bis(chlorophenyl)-2,2,2-trichloroethanol layer yielding DDTr-free 1,1-bis(chlorophenyl)-2,2,2-trichloroethanol.

18. The extraction process of claim 16 conducted at a temperature of from about $10°$ C. to about $60°$ C. wherein the first solvent is selected from the group consisting of methanol, ethanol, ($C_2$–$C_6$)diol or mixtures thereof containing up to about 30% water, wherein the second solvent is selected from the group consisting of ($C_5$–$C_{16}$)alkane, ($C_5$–$C_{15}$)alkene and mixtures thereof, wherein the weight of 1,1-bis(chlorophenyl)-2,2,2-trichloroethanol is from about 0.1 to about 1 of the first solvent.

19. The extraction process of claim 17 wherein the extraction is conducted at a temperature of from about $20°$ C. to about $40°$ C., the first solvent is aqueous methanol containing from about 9% to about 13% water, the concentration of the 1,1-bis(chlorophenyl)-2,2,2-trichloroethanol in the solution is from about 25% to about 35% and the second solvent is mixed heptanes.

20. A process for preparing DDTr-free 1,1-bis(chlorophenyl)-2,2,2-trichloroethanol comprising:

(a) at a temperature of from about $-5°$ C. to about $100°$ C., mixing DDTr-containing 1,1-bis(chlorophenyl)-2,2,2-trichloroethanol in a liquid-liquid extraction system comprising a first solvent selected form the group consisting of ($C_1$–$C_3$)alcohol, ($C_2$–$C_6$)diol, ($C_1$–$C_3$)organic acid, 4-hydroxy-3-methyl-2-butanone, acetone and mixtures thereof containing up to about 50% water and a second solvent selected from the group consisting of ($C_4$–$C_{20}$)alkane, ($C_4$–$C_{20}$)alkene, ($C_6$–$C_{20}$)alkadiene, ($C_6$–$C_{10}$) single ring aromatic and mixtures thereof, wherein the amount of 1,1-bis(chlorophenyl)-2,2,2-trichloroethanol is from about 0.01 to about 1.5 times the weight of the first solvent; and (b) allowing DDTr-free 1,1-bis(chlorophenyl)-2,2,2-trichloroethanol to distribute primarily in the first solvent and the DDTr's to distribute primarily in the second solvent.

21. The process of claim 20 wherein the first solvent containing DDTr-free 1,1-bis(chlorophenyl)-2,2,2-trichloroethanol is separated from the second solvent and the first solvent is removed to yield the DDTr-free 1,1-bis(chlorophenyl)-2,2,2-trichloroethanol.

22. The process of claim 20 wherein the first solvent is selected from the group consisting of methanol, ethanol, ($C_2$–$C_6$)diol and mixtures thereof containing up to about 30% water to obtain a solution having a 1,1-bis(chlorophenyl)-2,2,2-trichloroethanol concentration of from about 10% to about 50% and the second solvent is selected from the group consisting of ($C_5$–$C_{16}$)alkane, ($C_5$–$C_{15}$)alkene and mixtures thereof.

23. The process of claim 20 wherein the DDTr-containing 1,1-bis(chlorophenyl)-2,2,2-trichloroethanol is dissolved in the first solvent.

24. The process of claim 20 wherein the DDTr-containing 1,1-bis(chlorophenyl)-2,2,2-trichloroethanol is dissolved in a mixture of the first and second 25. A liquid-liquid extraction system for extracting DDTr's from 1,1-bis(chlorophenyl)-2,2,2-trichloroethonol comprising:

A first solvent selected from the group consisting of ($C_1$–$C_3$)alcohol, ($C_2$–$C_6$)diol, ($C_1$–$C_3$)organic acid, 4-hydroxy-3-methyl-2-butanone, acetone and mixtures thereof containing up to about 50% water;

A second solvent selected from the group consisting of ($C_4$–$C_{20}$)alkene, ($C_4$–$C_{20}$)alkane, ($C_6$–$C_{20}$)alkadiene, ($C_6$–$C_{10}$) single ring aromatic and mixtures thereof;

DDTr's; and 1,1-bis(chlorophenyl)-2,2,-trichloroethanol.

26. The liquid-liquid extraction system of claim 25 wherein the first solvent is selected from the group consisting of methanol, ethanol, ($C_2$–$C_6$)diol or mixtures thereof containing up to about 30% water, wherein the second solvent is selected from the group consisting of ($C_5$–$C_{16}$)alkane, ($C_5$–$C_{15}$)alkene and mixtures thereof, wherein the weight of 1,1-bis(chlorophenyl)-2,2,2-trichloroethanol is from about 0.1 to about 1 of the first solvent.

27. The liquid-liquid extraction system of claim 26 wherein the first solvent is methanol containing from about 7% to about 13% water.

28. The liquid-liquid extraction system of claim 27 wherein the second solvent is mixed heptanes.

29. The liquid-liquid extraction system of claim 28 wherein the first solvent is aqueous methanol containing from about 9% to about 13% water and wherein the amount of 1,1-bis(chlorophenyl)-2,2,2-trichloroethanol is from about 0.33 to about 0.54 the weight of the first solvent.

* * * * *

UNITED STATES PATENT AND TRADEMARK OFFICE
CERTIFICATE OF CORRECTION

PATENT NO. : 4,705,902

DATED : November 10, 1987

INVENTOR(S) : Nichols, Zabrodski, Mitra

It is certified that error appears in the above-identified patent and that said Letters Patent is hereby corrected as shown below:

Claim 24, Column 16, line 25: following "second" insert -- solvents. --

Signed and Sealed this

Twenty-first Day of June, 1988

Attest:

DONALD J. QUIGG

Attesting Officer

Commissioner of Patents and Trademarks